(12) United States Patent
Fuller

(10) Patent No.: US 7,264,934 B2
(45) Date of Patent: Sep. 4, 2007

(54) RAPID PARALLEL NUCLEIC ACID ANALYSIS

(75) Inventor: Carl W. Fuller, Berkeley Heights, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 35 days.

(21) Appl. No.: 11/255,683

(22) Filed: Oct. 21, 2005

(65) Prior Publication Data

US 2006/0051807 A1 Mar. 9, 2006

Related U.S. Application Data

(63) Continuation-in-part of application No. PCT/US2005/020378, filed on Jun. 9, 2005.

(60) Provisional application No. 60/578,789, filed on Jun. 10, 2004.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3

(58) Field of Classification Search ............. 435/6; 536/23.1, 24.3
See application file for complete search history.

(56) References Cited

U.S. PATENT DOCUMENTS 4,971,903 A * 11/1990 Hyman .................. 435/6
5,432,065 A * 7/1995 Fuller .................. 435/91.1
5,516,633 A * 5/1996 Fuller .................. 435/6
5,674,679 A 10/1997 Fuller
2002/0164629 A1* 11/2002 Quake et al. ........... 435/6
2003/0108867 A1* 6/2003 Chee et al. ............ 435/6

OTHER PUBLICATIONS

Sanger et al., DNA sequencing with chain -terminating inhibitors. PNAS 74(12) : 5463-5467 (1977).*
Pease et al., Light-generated oligonucleotide arrays for rapid DNA sequence analysis. PNAS 91: 5022-5026 (1994).*
Wang et al., Large-scale Identification, Mapping and Genotyping of Single-Nucleotide Polymorphisms in the Human ganome. Science 280 : 1077-1082 (1998).*
Pastinen et al., Minisequencing : A specific tool for DNA analysis and diagnostics on oligonucleotide arrays. Genome Research 7 : 606-614 (1997).*
Doublie et al. An opened and closed case for all polymerases. Structure 7(2) : R31-R35 (1999).*

* cited by examiner

*Primary Examiner*—Ethan Whisenant
(74) *Attorney, Agent, or Firm*—Yonggang Ji

(57) ABSTRACT

This invention provides methods for massive parallel nucleic acid analysis. A closed complex of nucleic acid template, nucleotide and polymerase can be formed during polymerase reaction, absent divalent metal ion. This is used to trap the nucleotide complementary to the next template nucleotide in the closed complex. Detection of the trapped nucleotide allows determination of the sequence of this next correct nucleotide. In this way, sequential nucleotides of a nucleic acid template can be identified, effectively determining the sequence. This method is applied to sequence multiple templates in parallel, particularly if they are immobilized on a solid support.

27 Claims, 11 Drawing Sheets

RAPID PARALLEL NUCLEIC ACID ANALYSIS

CROSS REFERENCE TO RELATED APPLICATIONS

This application is a continuation-in-part of international patent application number PCT/US2005/020378 filed Jun. 9, 2005, which claims priority to U.S. provisional patent application No. 60/578,789 filed Jun. 10, 2004. This application also claims priority to U.S. patent application Ser. Nos. 10/772,996 and 10/773,000 both filed Feb. 5, 2004; Ser. Nos. 10/651,362, 10/651,355, 10/651,582 and 10/651,558 all filed Aug. 29, 2003; Ser. No. 10/358,818 filed Feb. 5, 2003; Ser. Nos. 10/113,030 and 10/113,025 both filed Apr. 1, 2002; and Ser. No. 10/230,576 filed Aug. 29, 2002; the disclosures of which are incorporated herein by reference in their entirety.

FIELD OF THE INVENTION

The present invention relates generally to methods of high throughput, parallel sequencing of polynucleotides. More specifically, the invention relates to sequencing using an improved pyrosequencing technique that enables detection of each base of a polynucleotide template.

BACKGROUND OF THE INVENTION

DNA polymerases are enzymes which are useful in many recombinant DNA techniques, such as nucleic acid amplification by the polymerase chain reaction ("PCR"), self-sustained sequence replication ("3 SR"), and DNA sequencing. Thermostable DNA polymerases are particularly useful. Because heat does not destroy the polymerase activity, there is no need to add additional polymerase after every denaturation step.

In its catalytic cycle, the DNA polymerase-DNA complexes formed are known to undergo a rate-limiting, conformational transition from an 'open' to 'closed' state, upon binding of the 'correct' dNTP or ddNTP at the active site. In the 'closed' state, $Mg^{2+}$ (or other metal ion) mediates a rapid chemical step involving nucleophilic displacement of pyrophosphate by the 3' hydroxyl of the primer terminus. The enzyme returns to the 'open' state upon the release of pyrophosphate (PPi) and translocation initiates the next round of reaction. While the ternary complex (Enzyme-DNA-dNTP (or ddNTP) can form in the absence of $Mg^{2+}$ (or other metal ions), it is proficient in chemical addition of nucleotide only in the presence of $Mg^{2+}$ (or other metal ions). $Mg^{2+}$ (or other metal ion)-deficient conditions tend to lead to non-covalent (physical) sequestration of first 'correct' dNTP in a tight ternary complex (Doublie et al. (15 Feb. 1999) *Structure Fold. Des.*, 7(2):R31-5).

Pyrophosphate-based nucleic acid sequencing method (herein below referred to as pyrosequencing) is first described by Hyman (U.S. Pat. No. 4,971,903). This technique is based on the observation that pyrophosphate (PPi) can be detected by a number of assays. In a polymerase reaction, a sequencing primer is annealed to the template. If a nucleotide complements the next base in the template (i.e. next correct base 3' of the primer sequence), it is incorporated into the growing primer chain, and PPi is released. When only one of the four nucleotides is introduced into the reaction at a time, PPi is generated only when the correct nucleotide is introduced. Thus, the production of PPi reveals the identity of the next correct base. In this way, a sequence from a template is obtained or confirmed. Additional nucleotides of the sequence are obtained by cycling of the polymerase reaction, in the presence of a single nucleotide at a time.

Pyrosequencing does not require the separation or sizing of the reaction products by such methods as electrophoresis. It is capable of being performed in a massively parallel fashion. Pyrosequencing has been used successfully for a number of applications, including in clinical microbiology. A 96 well plate format is the most widely used format (see Biotage AB website). Recently, pyrosequencing has also been used to achieve ultra-high throughput sequencing, using template carrying microbeads deposited in microfabricated picoliter-sized reaction wells. Margulies et al., *Nature* advance online publication; published online 31 Jul. 2005, doi: 10.1038/nature03959.

There are several methods that can be used to detect PPi. One such assay uses two enzymes, ATP-sulfurylase and luciferase, to produce a light emission. ATP-sulfurylase generates ATP at the presence of PPi and adenosine-5'-phosphosulfate. Luciferase uses the ATP to convert luciferin to oxyluciferin, emitting a photon. Nyren et al., 151 Analytical Biochemistry 504 (1985). One problem of this reaction is that Luciferase is not absolutely specific for ATP, it can also work with dATP, and to a lesser extent may catalyze reaction with other nucleoside triphosphates as well. As such, the background can be high and non-specific reactions can happen, particularly when using dATP. Another problem with pyrosequencing is its difficulty in sequencing a stretch several consecutive nucleotides with the same base. When a stretch of the same base is present in a sequence, the polymerase continues adding the complementary nucleotides until the end of the stretch is reached and the next nucleotide requires a different base. The result is production of additional molecules of PPi, and increased light emission that is related to the number of nucleotides in the stretch. For shorter stretches of the same base, the measurement of increased light emission is sensitive enough to distinguish the length of the stretch but the accuracy of the estimate decreases as the length of the stretch increases.

Despite recent successes, the limitations of pyrosequencing remain. The current invention improves the pyrosequencing technology by overcoming these limitations.

SUMMARY OF THE INVENTION

This invention makes use of the above observation by use of the closed complex to freeze the polymerase activity during DNA synthesis, trapping the nucleotide which is complementary to the next template nucleotide, to allow the determination of the identity of the next correct nucleotide. It can then be identified either in place, as part of the complex, or as the pyrophosphate or dye-labeled polyphosphate is released from the complex when the reaction cycle is completed by the addition of divalent metal ion. In this way, sequential nucleotides of a DNA can be identified, effectively determining the DNA sequence. With sufficiently sensitive detection methods, this method can be applied both to single molecules of template nucleic acid or to collections of identical (or nearly identical) sequence such as PCR products or clones. If desired, multiple templates can be sequenced in parallel, particularly if they are effectively immobilized on a solid support such as plates or beads.

This invention combines pyrosequencing with closed complex formation to enable accurate, parallel sequencing of nucleic acid templates. It eliminates non-specificity of the pyrosequencing reaction, provides accurate sequence for each base of the polynucleotide sequence, and the nucleotides do not need to be labeled. When combined with microbeads and the picoliter-sized reaction well technology, it provides ultra-high throughput, non-ambiguous nucleic acid sequence at a short period of time.

DEFINITIONS

Figure 1:
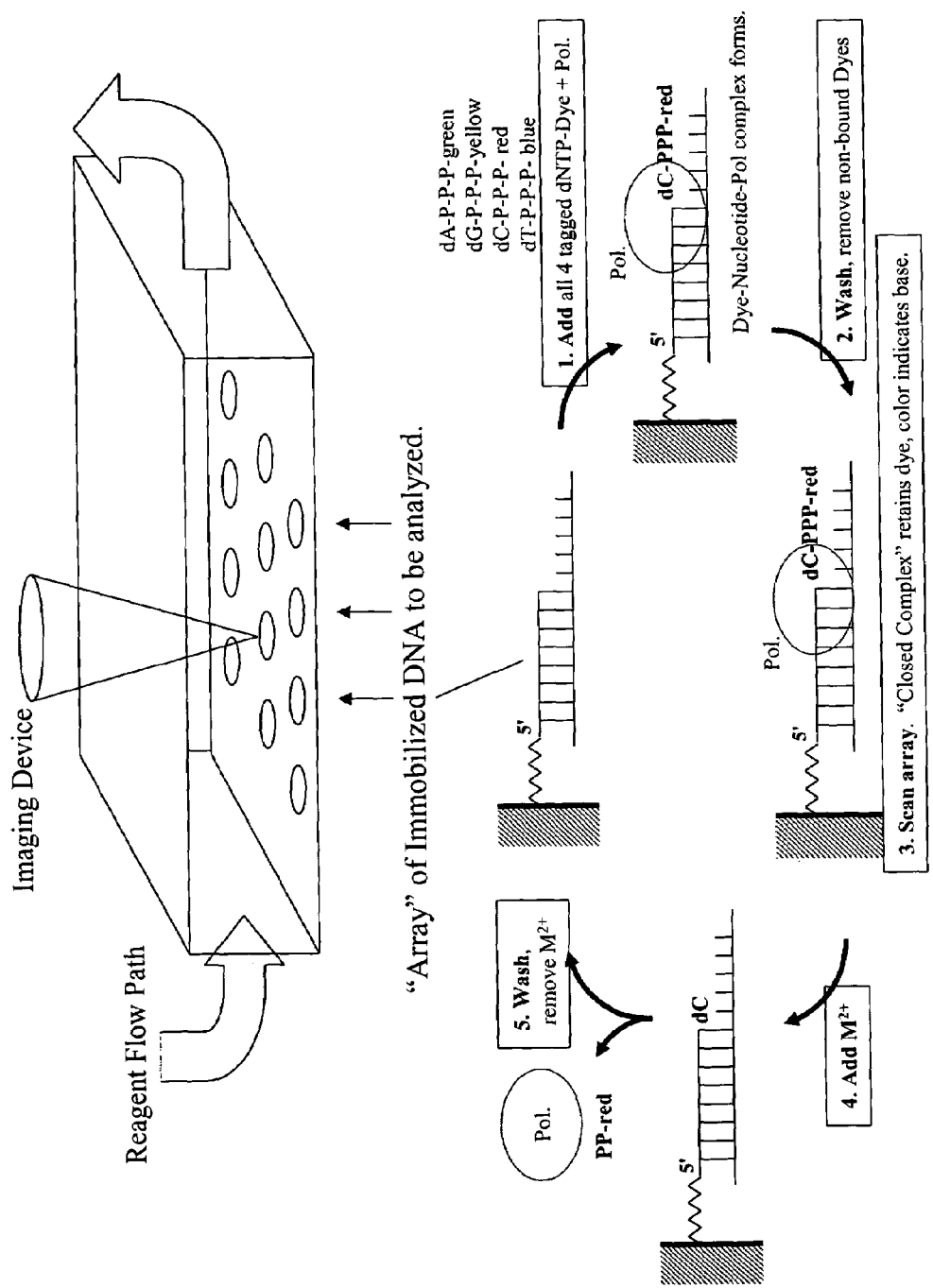
FIG. 1 depicts the reaction scheme for parallel sequencing by phosphate labeled nucleotides pausing at the closed complex stage of arrays of targets. Complex is stable for the full time scale of washing and scanning.

The term "nucleoside" as defined herein is a compound including a purine, deazapurine, pyrimidine or modified base linked to a sugar or a sugar substitute, such as a carbocyclic or acyclic moiety, at the 1' position or equivalent position and includes 2'-deoxy and 2'-hydroxyl, and 2',3'-dideoxy forms as well as other substitutions.

The term "nucleotide" as used herein refers to a phosphate ester of a nucleoside, wherein the esterification site typically corresponds to the hydroxyl group attached to the C-5 position of the pentose sugar. When referring to nucleotides that may form closed complexes with polymerases, templates and primers, the term specifically refers to triphosphates, tetraphosphates or esters of even longer polyphosphates which optionally may be labeled on the terminal phosphate with a colored, fluorescent, chemiluminescent, or other detectable moiety.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention.

The term "polymerase colony technology", or "polony", refers to technologies that perform multiplex amplification while maintaining spatial clustering of identical amplicons (see Harvard Molecular Technology Group and Lipper Center for Computational Genetics website). These include in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

The term "emulsion PCR" is also referred to as "ePCR". In emulsion PCR, a water-in-oil emulsion permits millions of non-interaction amplifications within a milliliter-scale volume (Tawfik and Griffiths, Nature Biotechnology 16, 652, July 1998; Ghadessy et al., PNAS 98, 4552, Apr. 10, 2001; Nakano et al., Journal of Biotechnology 102, 117, Apr. 24, 2003). Amplification products of individual compartments are captured via inclusion of beads bearing one of the PCR primers (Dressman et al., PNAS 100, 8817, Jul. 22, 2003; Margulies et al., *Nature* advance online publication; published online 31 Jul. 2005, doi: 10.1038/nature03959). Any single bead bears thousands of single-stranded copies of the same PCR product, whereas different beads bear the products of different compartmentalized PCR reactions.

DETAILED DESCRIPTION OF THE PREFERRED EMBODIMENTS

The present invention relates to methods of characterizing a polynucleotide in a sample wherein a convenient assay is used for monitoring RNA or DNA synthesis via nucleic acid polymerase activity. Nucleic acid polymerizing enzymes synthesize nucleic acid molecules via transfer of a nucleoside monophosphate from a nucleoside triphosphate (NTP) or deoxynucleoside triphosphate (dNTP) to the 3' hydroxyl of a growing oligonucleotide chain. This reaction also releases inorganic pyrophosphate. During the catalytic cycle of the polymerase reaction, DNA polymerase-DNA complexes formed are known to undergo a rate-limiting, conformational transition from an 'open' to 'closed' state, after binding of the 'correct' dNTP or ddNTP at the active site. In the absence of $Mg^{2+}$ (or other divalent cations), the ternary complexes (Enzyme-DNA-dNTP (or ddNTP) form, but the dNTP or ddNTP is not added to the growing nucleic acid molecule. This leads to non-covalent (physical) sequestration of the next, 'correct' nucleotide in the ternary complex. This invention makes use of this observation by use of this closed complex to freeze the polymerase during nucleic acid synthesis, trapping the nucleotide which is complementary to the next template nucleotide, to allow the determination of the identity of this next correct nucleotide. In this way, the sequence of a DNA or RNA molecule can be built up one nucleotide at a time.

In certain embodiments, the polymerase is a DNA polymerase, such as DNA polymerase I, II, or III or DNA polymerase α, β, γ, or terminal deoxynucleotidyl transferase or telomerase. In other embodiments, suitable polymerases include, but are not limited to, a DNA dependent RNA polymerase, a primase, or an RNA dependant DNA polymerase (reverse transcriptase). When RNA polymerase is used, a promoter sequence recognizable by the RNA polymerase is contained within the nucleic acid template or the primer sequence.

The nucleic acid template for sequencing in the methods of this invention may include an RNA or DNA template. When RNA is used as a template, the nucleic acid polymerizing enzyme can be a reverse transcriptase or an RNA polymerase.

The methods provided by this invention utilize a nucleoside polyphosphate, such as a deoxynucleoside polyphosphate, dideoxynucleoside polyphosphate, carbocyclic nucleoside polyphosphate, or acylic nucleoside polyphosphate analogue with a colorimetric dye, or a fluorescent label. The base in these nucleoside polyphosphate is selected from the group consisting of uracil, thymine, cytosine, 5-methylcytosine, guanine, 7-deazaguanine, hypoxanthine, 7-deazahypoxanthine, adenine, 7-deazaadenine, 2,6-diaminopurine and analogs thereof. To identify the bound nucleotide, the nucleotides are labeled with fluorescent dyes or colored dyes or other detectable tags. Suitable fluorescent dyes may be selected from the group consisting of a xanthene dye, a cyanine dye, a merrocyanine dye, an azo dye, a porphyrin dye, a coumarin dye, a bodipy dye and derivatives thereof. Suitable colored dyes may be selected from the group consisting of an azo dye, a merrocyanine, a cyanine dye, a xanthene dye, a porphyrin dye, a coumarin dye, a bodipy dye and derivatives thereof. These dyes are well known and are available from a number of commercial sources.

As described below, the methods of the current invention can be used to detect the sequence of a single molecule, or a homogeneous population of molecules. While the methods can be used to sequence unknown templates, it can also be used to confirm known sequences, identify single nucleotide polymorphisms, and perform single base extension reactions, amongst others. Cycling of the various steps of the methods leads to detection of additional sequence of the same molecule, one per cycle. When the aim is to sequence a single molecule, or a homogeneous population of molecules, the steps can be carried out in a sequential manner in a flow through or a stop-flow system. In such a flow through or stop flow system, the ternary complex of polymerase-template-nucleotide can be immobilized on beads, and the beads can be localized within a portion of a microchannel.

Alternatively, as described below, the methods of the current invention can also be adapted to perform massively parallel reactions, to sequence multiple templates at the same time. For multiplexed detections, the ternary complex of polymerase-template-nucleotide can be immobilized on beads within confined locations of a carrier (e.g. capillary), or they can be immobilized on the inner surface of a microchannel, or on a surface of a microscope slide or the like. The surface of a microscope slide can be a planar surface, or a coated surface. Additionally, the surface may comprise a plurality of microfeatures arranged in spatially discrete regions to produce a texture on the surface, wherein the textured surface provides an increase in surface area as compared to a non-textured surface.

The methods of the current invention require that the template-polymerase-nucleotide complex be immobilized to a support surface. It is contemplated that immobilization could occur before or after the formation of the ternary complex. When immobilization occurs before the formation of the ternary complex, one of several components could be immobilized. This includes the primer, the nucleic acid template, the nucleic acid polymerization enzyme, or the primer-template complex. When immobilization occurs after the formation of the ternary complex, the complex itself is immobilized. For multiplexed analysis of many sample templates, the species (the primer, the nucleic acid template, the nucleic acid polymerization enzyme, or the primer-template complex, or the ternary complex) immobilized can form an ordered pattern on the support surface. The species can also be immobilized randomly on the surface. However, each different species is located at a discrete location so that signal from any dye bound to one complex (or homogeneous population of complexes) is readily distinguishable from signal of another, adjacently immobilized complex.

The stability of the ternary complexes varies. As shown below, FY7 DNA polymerase (U.S. Pat. No. 6,479,267) can form a very stable complex with the template and dye-labeled nucleotide. In this case, step by step sequencing of a single molecule of nucleic acid using labeled dNTPs is possible. This method, when used in a multiplexed format, could allow sequencing of tens of thousands of templates simultaneously in a very short time or sequencing long regions of DNA. These methods are described in more detail below.

In one embodiment of the method of characterizing a target region of a nucleic acid template, the steps include: a) initiating a nucleic acid polymerization reaction on a support, by forming a reaction mixture, the reaction mixture including a nucleic acid template, a primer, a nucleic acid polymerizing enzyme, and four terminal-phosphate-labeled nucleotides each containing a distinct label, wherein a component of the reaction mixture or a first complex of two or more of the components, is immobilized on the support, and the component or components are selected from the group consisting of the nucleic acid template, primer, and nucleic acid polymerizing enzyme, and wherein each of the four terminal-phosphate-labeled nucleotides contains a base complementary to each of the four naturally occurring bases; b) progressing the nucleic acid polymerization reaction by incubating the reaction mixture to form a second complex comprising the nucleic acid template, primer, nucleic acid polymerizing enzyme, and a terminal-phosphate-labeled nucleotide, wherein the terminal-phosphate-labeled nucleotide contains a base complementary to the template base at the site of polymerization; c) removing unbound terminal-phosphate-labeled nucleotides and other components of the reaction mixture; d) detecting the label of the terminal-phosphate-labeled nucleotide from the second complex; and therefore identifying the nucleotide bound.

In this embodiment, the template used for the nucleic acid polymerase reaction is a single molecule, or a homogeneous population of molecules. For sequencing additional bases after the first base, in addition to steps (a) through (d) above, the following steps are performed: e) adding a divalent cation to complete the polymerization reaction (now in the absence of free nucleotide); f) removing the divalent cation and other end products from the polymerization reaction; and g) repeating steps (a) through (f) for determining additional nucleotides in sequence.

Optionally, an excess of a chelating agent (e.g. EDTA) can be added in any or all of steps (a) through (d) and in particular step (f) to sequester any residual divalent cation that might be present in the reaction mixture. It is contemplated that a chelating agent can be added to each of the methods disclosed in the current invention, for the same purpose, whenever there is a need. Addition of the chelating agent does not interfere with the formation of the ternary complex of template-polymerase-dNTP (or ddNTP). This is experimentally shown in the examples provided below. These chelating agents are removed with the addition of the divalent cation (e.g. manganese or magnesium), which enables the completion of the polymerase reaction cycle.

When the scheme of the above embodiment is used to characterize a nucleic acid sequence of a nucleic acid template, sometimes less than all four terminal-phosphate-labeled nucleotides can be used. For example, only two terminal-phosphate-labeled nucleotides are needed when characterizing a bi-allelic SNP of a sample template. Only a single terminal-phosphate-labeled nucleotide is needed when determining the presence of a particular nucleic acid sequence in a sample template.

These embodiments, when used in a multiplexed format, could allow sequencing of tens of thousands of templates simultaneously in a very short time or sequencing long regions of DNA. Therefore, in one embodiment for parallel characterization of a target region of a plurality of nucleic acid templates provided herein, the steps include: a) immobilizing a plurality of primers or nucleic acid templates on a support structure, wherein each primer or template contains a unique sequence and wherein each primer (or multiple copies of the same primer) or template is localized to an identifiable, discrete location on the support structure; b) initiating a plurality of nucleic acid polymerization reactions on the support structure, by forming a reaction mixture, the reaction mixture including the plurality of primers, the plurality of nucleic acid templates, a nucleic acid polymerizing enzyme, and at least one terminal-phosphate-labeled nucleotides each containing a distinct label, wherein each of the terminal-phosphate-labeled nucleotides contains a base complementary to each of the four naturally occurring bases; c) progressing the nucleic acid polymerization reactions by incubating the reaction mixture to form a plurality of complexes, each comprising one of the plurality of primers, one of the plurality of nucleic acid template, the nucleic acid polymerizing enzyme, and a terminal-phosphate-labeled nucleotide, wherein the terminal-phosphate-labeled nucleotide contains a base complementary to the template base at the site of polymerization; d) removing unbound terminal-phosphate-labeled nucleotides and other components of the reaction mixture; e) detecting, at each of the identifiable, discrete locations, the distinct label of the terminal-phosphate-labeled nucleotide from the complex. In addition, the detected results are optionally recorded to data storage media; and the results converted to one of the four nucleotide sequences.

In this method, each of the template (or primer) used for the nucleic acid polymerase reaction is a single molecule or a homogeneous population of molecules. For sequencing additional bases after the first base, in addition to steps (a) through (e) above, the following steps are performed: f) adding a divalent cation to complete the polymerization reactions; g) removing the divalent cation and other end products from the polymerization reactions; and h) repeating steps (a) through (g) for the characterization of each additional nucleotide of the plurality of nucleic acid templates. FIG. 1 depicts the multiplexing embodiment of the invention.

In another embodiment of the method of sequencing a target region of a nucleic acid template provided herein, the steps include: (a) initiating a nucleic acid polymerization reaction on a support, by forming a reaction mixture, the reaction mixture including a nucleic acid template, a primer, a nucleic acid polymerizing enzyme, and at least one terminal-phosphate-labeled nucleotides each containing a distinct label, wherein a component of the reaction mixture or a first complex of two or more of the components, is immobilized on the support, and the component or components are selected from the group consisting of the nucleic acid template, the primer, and the nucleic acid polymerizing enzyme, and wherein each of the at least one terminal-phosphate-labeled nucleotides contains a base complementary to the four naturally occurring bases; (b) progressing the nucleic acid polymerization reaction by incubating the reaction mixture to form a second complex comprising the nucleic acid template, primer, nucleic acid polymerizing enzyme, and a terminal-phosphate-labeled nucleotide, wherein the terminal-phosphate-labeled nucleotide contains a base complementary to the template base at the site of polymerization; (c) removing unbound terminal-phosphate-labeled nucleotides and other components of the reaction mixture; (d) adding a divalent cation to complete the polymerization reaction; (e) detecting the label of the terminal-phosphate-labeled nucleotide from the second complex; (f) identifying the nucleotide bound; (g) removing the divalent cation and other end products from the polymerization reaction; and (h) repeating steps a) through g) for determining each additional nucleotide in sequence. In this embodiment, the template used for the nucleic acid polymerase reaction is a single molecule, or a homogeneous population of molecules.

Figure 2:
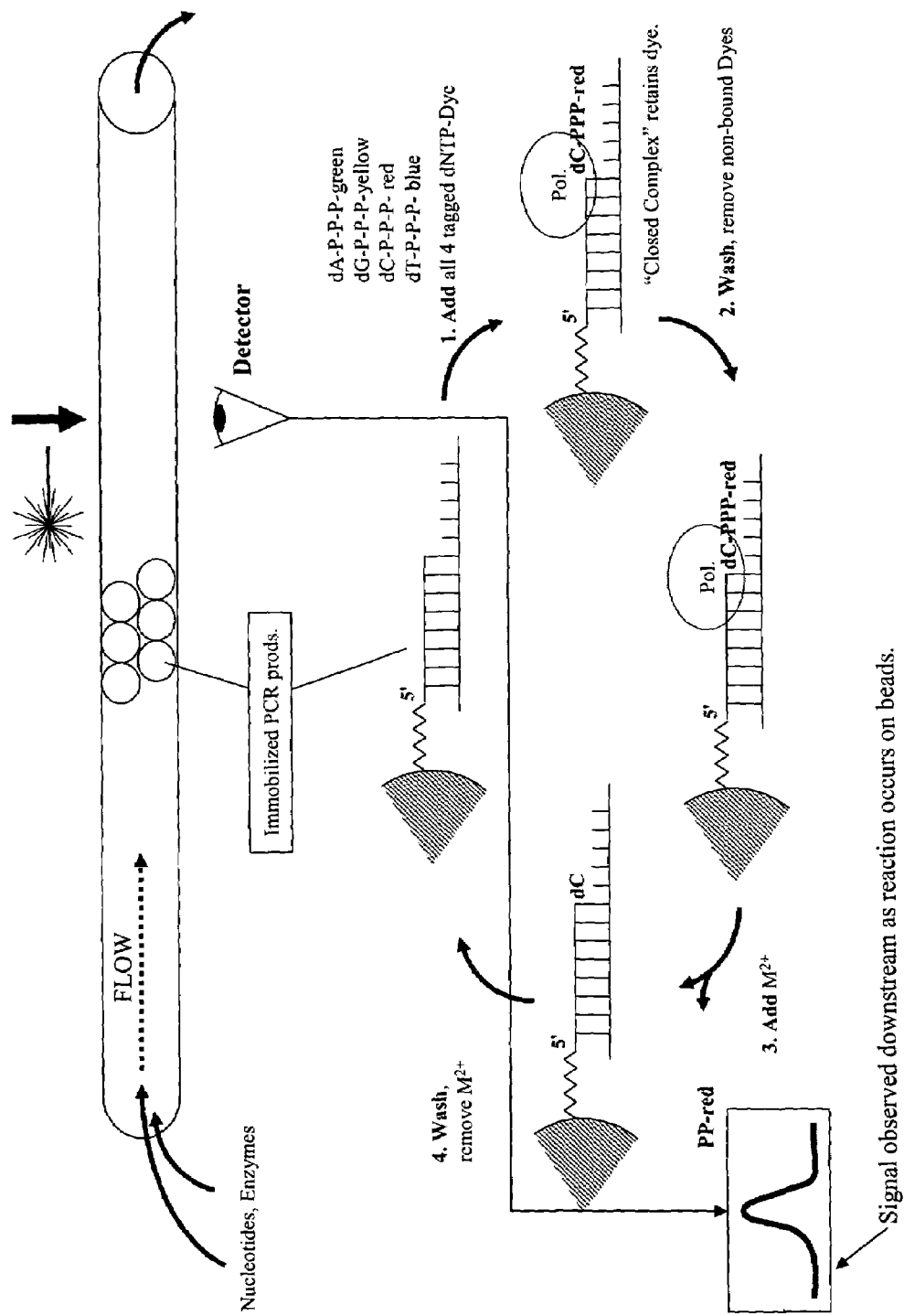
FIG. 2 depicts the reaction and detection scheme for sequencing by phosphate labeled nucleotides pausing at the closed complex stage. Complex is stable for the full time scale of washing and detection.

The present invention further provides methods of sequencing a target sequence using the steps described above in a continuous flow or a stop-flow system, where the immobilized material is held in place by any one of the means known in the art and different reagents and buffers are pumped in to the system at one end and exit the system at the other end. Reagents and buffers may flow continuously or may be held in place for certain time to allow for the polymerization reaction to proceed. An illustration of the process is presented in FIG. 2. As shown in FIG. 2, beads within a microchannel provide support surface for the immobilization of the reaction complexes. As the buffers and reagents move along through the system, the dye released from the polymerase reaction moves directionally toward the exiting end of the microchannel. Detection of the dye labeled dNTP (or ddNTP) captured by the polymerase can be performed at a number of locations within the system, even after the dye is released from the nucleotide by the addition of divalent cation. These locations include the one where the beads are held (before or after the additional of the divalent cation), or downstream of where the beads are held but before the dyes exit the system. Alternatively, the dye containing solution can be first collected as it exits the system, and then detected.

If the stability of the closed complex (which may be subject to reaction conditions such as pH or temperature) is such that it is only seconds instead of minutes, the method can still be used to sequence single molecules. The detection technique involves observing microscopic "flashes" of fluorescence at the site of the complex which would indicate the temporary (duration of seconds), binding of the next correct nucleotide (labeled), (resulting in a colored "glittering" of the DNA-DNA polymerase complex). Since the "closed complex" that is only formed with the next correct nucleotide, has at least 10-times longer lifetime than an open complex containing the incorrect next nucleotide, its fluorescence will dominate the observed signal at the site of the complex. This should be readily distinguishable from fluorescence of free nucleotide which will only remain at the site of the complex a very brief time, particularly when present at low concentration. While terminal phosphate labeled dNTPs or ddNTPs could be used, so could base labeled ddNTPs. The result is the identification of the single "next" nucleotide occurring at the 3' end of the primer. This information alone could be useful if primers are chosen to be adjacent to interesting loci such as SNPs.

These methods are described in more detail below. In one embodiment of the method of analyzing a target region of a nucleic acid template provided herein, the steps include: a) initiating a nucleic acid polymerization reaction on a support, by forming a reaction mixture, the reaction mixture including a nucleic acid template, a primer, a nucleic acid polymerizing enzyme, and at least one nucleotides each containing a distinct label, wherein a component of the reaction mixture or a first complex of two or more of the components, is immobilized on the support, and the component or components are selected from the group consisting of the nucleic acid template, the primer, and the nucleic acid polymerizing enzyme, and wherein one of the at least one labeled nucleotides contains a base complementary to the template base at the site of polymerization; b) incubating the reaction mixture to form a second complex comprising the nucleic acid template, primer, nucleic acid polymerizing enzyme, and one of the at least one labeled nucleotide, wherein the labeled nucleotide contains a base complementary to the template base at the site of polymerization, and wherein the labeled nucleotide is in dynamic equilibrium within the second complex; c) detecting the label of the labeled nucleotide; and d) identifying the nucleotide based on the detected distinctive label.

In this method, the template used for the nucleic acid polymerase reaction is a single molecule, or a homogeneous population of molecules. For analyzing additional bases after the first base, in addition to steps (a) through (d) above, the following steps are performed: e) removing the at least one labeled nucleotides and other components from the reaction mixture; f) adding, to the reaction mixture, a nucleic acid polymerizing enzyme, a divalent cation, and a nucleotide containing the base complementary to the template base at the site of polymerization; g) completing the polymerization reaction by incubating the reaction mixture for a period of time; h) removing the divalent cation, nucleotide and other end products from the polymerization reaction; and i) repeating steps (a) through (h) for each additional nucleotide to be analyzed.

The drawback to this method would be that runs of the same bases could not be fully sequenced. For example, a sequence of GGGTTTCCTCTC (SEQ ID NO: 1) would be read as GTCTCTC (SEQ ID NO: 2), but this information is useful in many situations, particularly when confirming known sequence.

These methods, when used in a multiplexed format, could allow sequencing of tens of thousands of templates simultaneously in a very short time or sequencing long regions of DNA. Therefore, in another embodiment for parallel characterization of a target region of a plurality of nucleic acid templates provided herein, the steps include: a) immobilizing a plurality of primers on a support structure, wherein each primer contains a unique sequence and wherein each primer (or multiple copies of each primer) is localized to an identifiable, discrete location on the support structure; b) initiating a plurality of nucleic acid polymerization reactions on the support structure, by forming a reaction mixture, the reaction mixture including the plurality of immobilized primers, a plurality of nucleic acid templates, a nucleic acid polymerizing enzyme, and four labeled nucleotides each containing a distinct label, wherein each of the four labeled nucleotides contains a base complementary to each of the four naturally occurring bases; c) incubating the reaction mixture to form a plurality of second complexes, each comprising one of the plurality of immobilized primers, one of the plurality of nucleic acid templates, the nucleic acid polymerizing enzyme, and a labeled nucleotide, wherein the labeled nucleotide contains a base complementary to the template base at the site of polymerization, and wherein said labeled nucleotide is in dynamic equilibrium within the second complex; d) detecting, at each of the identifiable, discrete locations, the label of the labeled nucleotide; e) recording data obtained from step d) to a data storage media; and f) characterizing the target sequence of each of the plurality of nucleic acid templates by converting the recorded data to one of the four nucleotides.

In this method, each of the template (or primer) used for the nucleic acid polymerase reaction is a single molecule or a homogeneous population of molecules. The drawback to this method would be that runs of the same bases could not be fully sequenced. For example, as stated above, a sequence of GGGTTTCCTCTC (SEQ ID NO: 1) would be read as GTCTCTC (SEQ ID NO: 2), but this information is useful in many situations. While this method only provides sequence information of the first base, cycling of a similar method can provide sequence information for multiple bases of each template.

Another method that could be used in a multiplexed format will also allow sequencing of tens of thousands of templates simultaneously in a very short time or sequencing long regions of DNA. This method could be used to obtain sequence of multiple bases from the same template, with the same limitation. Runs of the same bases could not be easily detected (e.g. GGGTTTCCTCTC (SEQ ID NO: 1)) would be read as GTCTCTC (SEQ ID NO: 2). Therefore, in another embodiment for parallel characterization of a target region of a plurality of nucleic acid templates provided herein, the steps include: a) immobilizing a plurality of primers on a support structure, wherein each primer contains a unique sequence and wherein each primer is localized to an identifiable, discrete location on the support structure; b) initiating a plurality of nucleic acid polymerization reactions on the support structure, by forming a reaction mixture, the reaction mixture including the plurality of immobilized primers, a plurality of nucleic acid templates, a nucleic acid polymerizing enzyme, and one labeled nucleotides; c) incubating the reaction mixture to form a plurality of second complexes, each comprising one of the plurality of immobilized primers, one of the plurality of nucleic acid templates, the nucleic acid polymerizing enzyme, and the labeled nucleotide, wherein the labeled nucleotide contains a base complementary to the template base at the site of polymerization, and wherein the labeled nucleotide is in dynamic equilibrium within the second complex; d) detecting, at the identifiable, discrete locations, the label of the labeled nucleotide; e) recording data obtained from the detecting step to a data storage media; f) removing labeled nucleotides and other components from the reaction mixture; g) adding, to the reaction mixture, a nucleic acid polymerizing enzyme, a divalent cation, and an unlabeled equivalent of the labeled nucleotide; h) completing the polymerization reaction by incubating the reaction mixture for a period of time; i) removing the divalent cation and other end products from the polymerization reaction; j)

repeating steps a) through i) with one of the other three nucleotides, until all four nucleotides are tested; and k) repeating steps a) through j) for determining additional nucleotide sequences.

The data (dye label information) obtained from this method are processed in a computer system with an appropriate algorithm. The data are converted to sequence information of each of the four nucleotides, either instantaneously as the data is generated, or at the end of the experimental reactions. The sequences are next assembled for each of the plurality of nucleic acid templates. It is noted that the order of addition of labeled nucleotides can occur in a preset cycle, but it is not essential.

The following example illustrates the process for determining the sequence of two template nucleic acid molecules using the above method. Assuming the sequences to be analyzed are (a) GGGTTTCCTCTC (SEQ ID NO: 1) and (b) CTCTCCTTTTGGG (SEQ ID NO: 3) and nucleotides complementary to G, C, A, T, are added in this order. In the first of the cycle of step (O) above, a nucleotide complementary to G is added. A signal is detected from the location where the next nucleotide base on the template is a G (in this case SEQ ID NO: 1). A signal is not detected from the location where the next nucleotide base on the template is not a G (in this case SEQ ID NO: 3, which contains a next C). The information is recorded to a data storage media. In the second of the cycle, a nucleotide complementary to C is added. Now a signal is detected from the location that contains the template of SEQ ID NO: 3 (with a next C). A signal is not detected from the location that contains the template of SEQ ID NO: 1 (with a next T). Again, this information is recorded to a data storage media. As the cycles continue, data regarding the two templates are obtained. If a full cycle of reactions with each of the four nucleotides gives no detectable data, it signals that the template sequence is completely sequenced. The end result from the reactions, for the template of SEQ ID NO: 1, reads as GTCTCTC (SEQ ID NO: 2), while the end result from the reactions, for the template of SEQ ID NO: 3, reads as CTCTCTG (SEQ ID NO: 4).

If the stability of the closed complex is such that it can only be measured from seconds to a few minutes, the method can still be used to sequence single molecules. The detection technique involves observing microscopic "flashes" at the site of the complex which would indicate the temporary (duration of seconds to minutes), binding of the next correct nucleotide (labeled). While terminal phosphate labeled dNTPs or ddNTPs could be used, so could base labeled ddNTPs. The only drawback to this technique would be that runs of the same bases could not be fully sequenced. For example, a sequence of GGGTTTCCTCTC (SEQ ID NO: 1) would be read as GTCTCTC (SEQ ID NO: 2), but this information is useful.

These methods are described in more detail below. In one embodiment of the method of analyzing a target region of a nucleic acid template provided herein, the steps include: (a) initiating a nucleic acid polymerization reaction on a support, by forming a reaction mixture, the reaction mixture including a nucleic acid template, a primer, a nucleic acid polymerizing enzyme, and at least one nucleotides each containing a distinct label, wherein a component of the reaction mixture or a first complex of two or more of the components, is immobilized on the support, and the component or components are selected from the group consisting of the nucleic acid template, primer, and nucleic acid polymerizing enzyme, and wherein one of the at least one labeled nucleotides contains a base complementary to the template base at the site of polymerization; (b) incubating the reaction mixture to form a second complex comprising the nucleic acid template, primer, nucleic acid polymerizing enzyme, and one of the at least one labeled nucleotide, wherein the labeled nucleotide contains a base complementary to the template base at the site of polymerization, and wherein the labeled nucleotide is in dynamic equilibrium within the second complex; (c) removing, from the reaction mixture, un-bound portion of the at least one labeled nucleotides and other components of the reaction mixture; (d) detecting the label of the labeled nucleotide; and (e) identifying the nucleotide sequence based on the detected distinctive label.

In this method, the template used for the nucleic acid polymerase reaction is a single molecule, or a homogeneous population of molecules. For analyzing additional bases after the first base, in addition to steps (a) through (e) above, the following steps are performed: (f) adding, to the reaction mixture, a nucleic acid polymerizing enzyme, a divalent cation, and an un-labeled nucleotide containing identified base sequence; (g) completing the polymerization reaction by incubating the reaction mixture for a period of time; (h) removing the divalent cation and other end products from the polymerization reaction; and (i) repeating steps (a) through (h) for each additional nucleotide to be sequenced. If the labeled nucleotides are base labeled, it is preferred that an additional wash step is performed before step (f) to get rid of the template-primer-polymerase complex captured labeled nucleotides.

Figure 3:
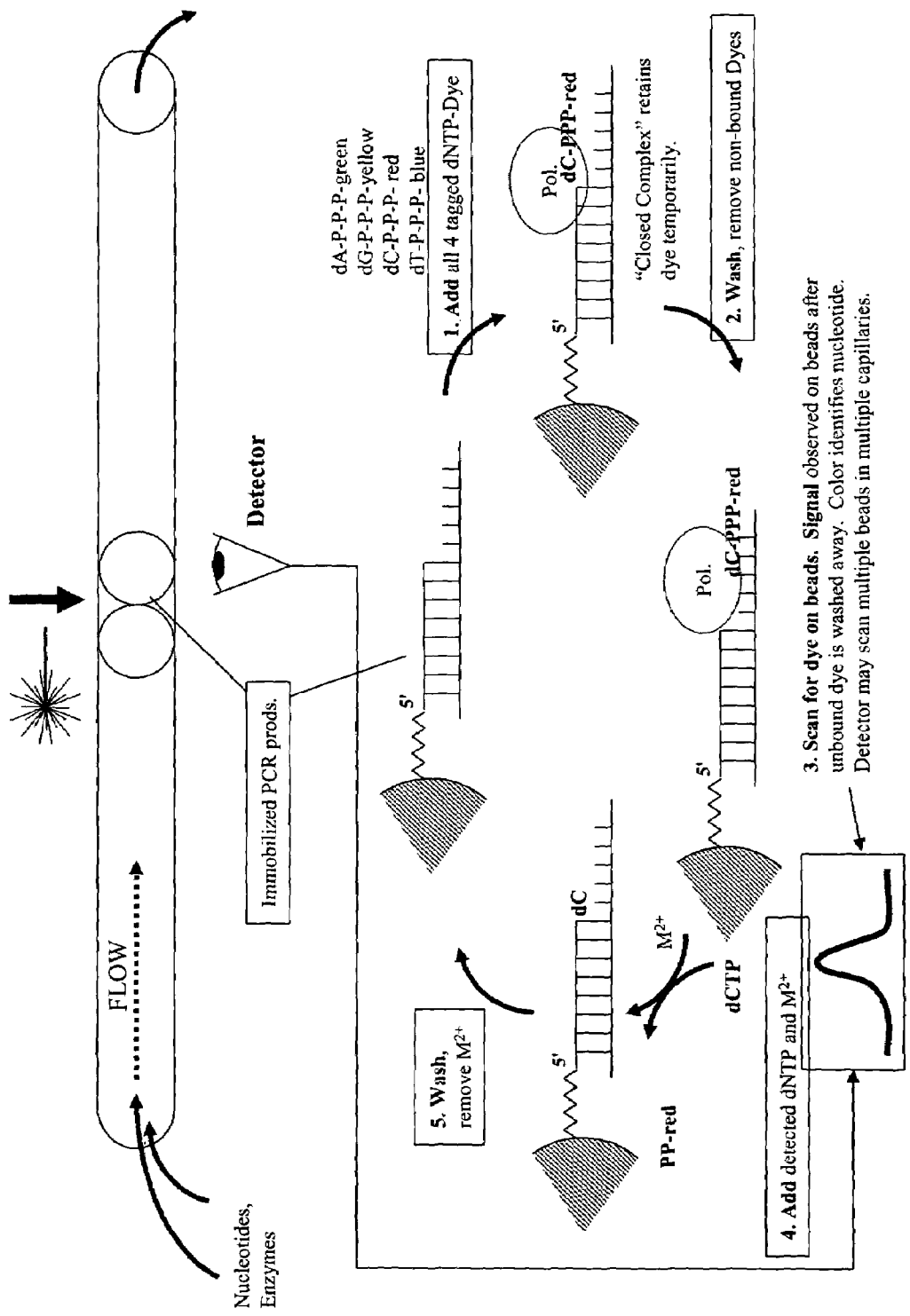
FIG. 3 depicts the reaction and detection scheme for sequencing by phosphate labeled nucleotides pausing at the closed complex stage. Complex is only partially stable for the full time scale of washing and detection. Sequence obtained will not distinguish multiples of a base (A, AA, AAA etc.) in the sequence.

FIG. 3 depicts the reaction and detection scheme for sequencing by phosphate labeled nucleotides pausing at the closed complex stage as detailed above. The only drawback of this method is that runs of the same bases could not be fully sequenced. For example, as stated above, a sequence of GGGTTTCCTCTC (SEQ ID NO: 1) would likely be read as GTCTCTC (SEQ ID NO: 2), but this information is useful in many situations.

These methods, when used in a multiplexed format, could allow sequencing of tens of thousands of templates simultaneously in a very short time or sequencing long regions of DNA. Therefore, in another embodiment for parallel characterization of a target region of a plurality of nucleic acid templates provided herein, the steps include: (a) immobilizing a plurality of primers on a support structure, wherein each primer contains a unique sequence and wherein each primer (or multiple copies of each primer) is localized to an identifiable, discrete location on the support structure; (b) initiating a plurality of nucleic acid polymerization reactions on the support structure, by forming a reaction mixture, the reaction mixture including the plurality of immobilized primers, a plurality of nucleic acid templates, a nucleic acid polymerizing enzyme, and four labeled nucleotides each containing a distinct label, wherein each of the four labeled nucleotides contains a base complementary to each of the four naturally occurring bases; (c) incubating the reaction mixture to form a plurality of second complexes, each comprising one of the plurality of immobilized primers, one of the plurality of nucleic acid templates, the nucleic acid polymerizing enzyme, and a labeled nucleotide, and the labeled nucleotide contains a base complementary to the template base at the site of polymerization, and the labeled nucleotide is in dynamic equilibrium within the second complex; (d) removing, from the reaction mixture, un-bound labeled nucleotides and other components of the reaction mixture; (e) detecting, at each of the identifiable, discrete locations, the label of the labeled nucleotide; (f) recording information obtained about the label to a data storage media; and (g) characterizing the target nucleotide sequence of each of the plurality of nucleic acid templates by converting the recorded data to one of four nucleotides.

Figure 4:
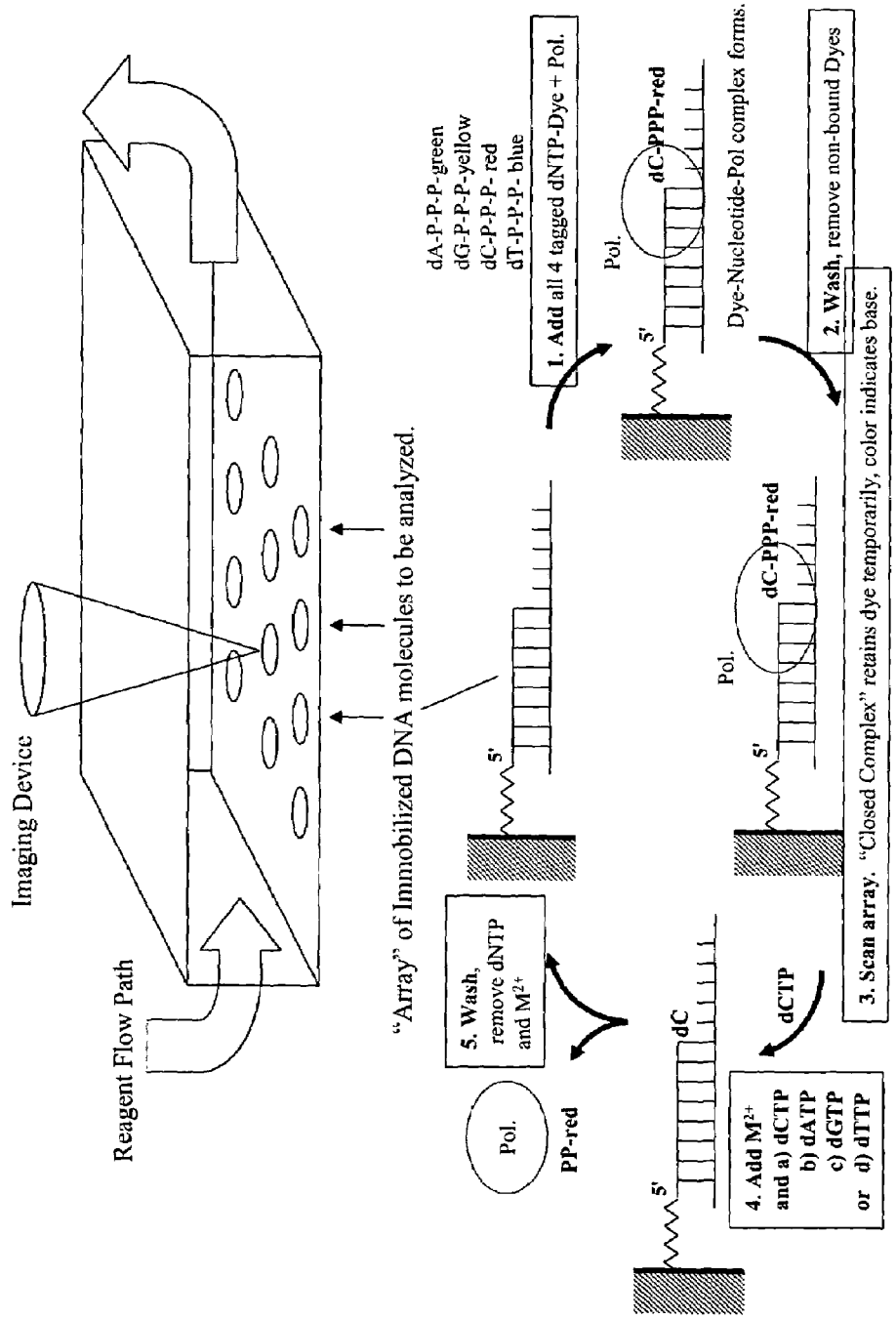
FIG. 4 depicts the reaction scheme for parallel sequencing by phosphate labeled nucleotides pausing at the closed complex stage of arrays of targets. Complex is only partially stable for the full time scale of washing and detection. Sequence obtained will not distinguish multiples of a base (A, AA, AAA etc.) in the sequence.

In this method, each of the template (or primer) used for the nucleic acid polymerase reaction is a single molecule or a homogeneous population of molecules. FIG. 4 depicts the reaction scheme for parallel sequencing as detailed hereinabove. The drawback to this method would be that runs of the same bases could not be fully sequenced. For example, as stated above, a sequence of GGGTTTCCTCTC (SEQ ID NO: 1) would be read as GTCTCTC (SEQ ID NO: 2), but this information is useful in many situations. While this method only provides sequence information of the first base, cycling of a similar method can provide sequence information for multiple bases of each template.

Another method that could be used in a multiplexed format will also allow sequencing of tens of thousands of templates simultaneously in a very short time or sequencing long regions of DNA. This method could be used to obtain sequence of multiple bases from the same template. Therefore, in another embodiment for parallel characterization of a target region of a plurality of nucleic acid templates provided herein, the steps include: (a) immobilizing a plurality of primers on a support structure, wherein each primer contains a unique sequence and wherein each primer is localized to an identifiable, discrete location on the support structure; (b) initiating a plurality of nucleic acid polymerization reactions on the support structure, by forming a reaction mixture, including the plurality of immobilized primers, a plurality of nucleic acid templates, a nucleic acid polymerizing enzyme, and at least one labeled nucleotides; (c) incubating the reaction mixture to form a plurality of second complexes, each comprising one of the plurality of immobilized primers, one of the plurality of nucleic acid templates, the nucleic acid polymerizing enzyme, and one of the at least one labeled nucleotide, each of the labeled nucleotide contains a base complementary to the template base at the site of polymerization, and the labeled nucleotide is in dynamic equilibrium within the second complex; (d) removing, from the reaction mixture, unbound labeled nucleotides and other components of the reaction mixture; (e) detecting, at the identifiable, discrete locations, the label of the labeled nucleotide; (f) recording data obtained from the detecting step to a data storage media; (g) adding, to the reaction mixture, a nucleic acid polymerizing enzyme, a divalent cation, and an un-labeled equivalent of the labeled nucleotide; (h) completing the polymerization reaction by incubating the reaction mixture for a period of time; (i) removing the divalent cation and other end products from the polymerization reaction; (O) repeating steps a) through i) with one of the other three nucleotides, until all four nucleotides are tested; and (k) repeating steps a) through j) for determining additional nucleotide sequences. If the labeled nucleotides are base labeled, it is preferred that an additional wash step is performed before step (g) to get rid of the template-primer-polymerase complex captured labeled nucleotides.

The data (dye label information) obtained from this method are processed in a computer system with an appropriate algorithm. The data are converted to sequence of each of the four nucleotides, either instantaneously as the data is generated, or at the end of the experimental reactions. The sequences are next assembled for each of the plurality of nucleic acid templates. It is noted that the order of addition of labeled nucleotides can occur in a preset cycle, but it is not essential.

We describe herein below embodiments wherein a step featuring closed complex formation in the absence of divalent metal ion is added to the pyrosequencing technique. This novel combination enables accurate, parallel sequencing of nucleic acid templates. It eliminates non-specificity of the pyrosequencing reaction, provides accurate sequence for each base of the polynucleotide sequence, and the nucleotides do not need to be labeled. When combined with microbeads and the picoliter-sized reaction well technology, it provides ultra-high throughput, non-ambiguous nucleic acid sequence.

An embodiment of the invention provides a method for parallel sequencing of a plurality of nucleic acid templates, comprising the following steps. First, a plurality of primed nucleic acid templates are immobilized on a support structure, wherein each primed template includes a template and a primer, and is localized to an identifiable, discrete location on the support structure. Second, a plurality of closed-complex complexation reactions are initiated on the support structure, by forming a reaction mixture including the plurality of primed nucleic acid templates, a nucleic acid polymerizing enzyme, and at least one nucleotide to form a plurality of closed complexes, each comprising one of the plurality of primed templates, a nucleic acid polymerizing enzyme, and a nucleotide that contains a base that complements the template base at the site of polymerization. After the formation of the closed-complex, unbound nucleotide and other unbound components are removed from the reaction mixture. A divalent cation is added to complete the reactions—either before or after the detection of the incorporated nucleotide for each nucleic acid template—depending on the detection method used. The incorporated nucleotide is detected directly, or through the detection of polymerization reaction by-product, at each of said identifiable, discrete locations. After detection, the divalent cation and other end products are removed from the local vicinity of the support structure; and the protocol is repeated to initiate another round of complex formation followed by polymerization reaction, for the sequencing of each additional nucleotide of the templates.

As described earlier, during the catalytic cycle of the polymerase reaction, the DNA polymerase-DNA complex formed is known to undergo a rate-limiting, conformational transition from an 'open' to 'closed' state, after binding of the 'correct' dNTP or ddNTP at the active site. In the absence of $Mg^{2+}$ (or other divalent cations), the ternary complexes (Enzyme-DNA-dNTP (or ddNTP) form, but the dNTP or ddNTP is not added to the growing nucleic acid molecule. This leads to non-covalent (physical) sequestration of the next, 'correct' nucleotide in the ternary complex. This invention makes use of this observation by use of this closed complex to freeze the polymerase during nucleic acid synthesis, trapping the nucleotide which is complementary to the next template nucleotide, to allow the determination of the identity of this next correct nucleotide. In this way, the sequence of a DNA or RNA molecule can be determined, building up one nucleotide at a time.

One of the enzymes that is shown in the examples section to form a closed complex is the FY7 DNA polymerase (U.S. Pat. No. 6,479,267), although many other polymerases can also be used. FY7 DNA polymerase can form a very stable complex with the primed template and nucleotide. In this case, step by step sequencing of a nucleic acid template is possible. Examples of additional enzymes are described earlier in the specification. The nucleic acid template for sequencing using the methods of this invention may include an RNA or DNA template. When RNA is used as a template, the nucleic acid polymerizing enzyme can be a reverse transcriptase or an RNA polymerase. A commonly used divalent cation for the progression of the polymerization reaction is that of magnesium ($Mg^{2+}$), although other divalent cations such as $Mn^{2+}$ can be used as well. To ensure that the divalent cation is absent while the closed complex forms, EDTA or other chelator can be added to the reaction mixtures that lack divalent cation.

The methods provided by this invention utilize nucleoside polyphosphates, or analogues. These nucleoside polyphosphates are either un-labeled, or terminal phosphate labeled with a chemiluminescent moiety, a colorimetric dye, or a fluorescent label, any of which may change physiochemical properties when released from the phosphate portion of the nucleotide. Depending on the presence or absence of a label, and the nature of the label present, different strategies are used to identify the bound nucleotide.

It is known that nucleoside polyphosphates (nucleotides) can carry a terminal phosphate label, and that these labeled nucleotides can be used to make polynucleotides by catalysis with a nucleic acid polymerase. When it is desirable to detect a nucleotide while it is held by polymerase in the closed complex state, a florescent or colorimetric label is chosen. The individual nucleotides can be labeled with distinct dyes, so all four nucleotides can be included in a process that selects out single nucleotides for detection and identification. Alternatively, the nucleotides can carry the same dye label. However, in this situation, only a single nucleotide is introduced at a time, so that label signal can be correctly assigned for a specific base if desired. To determine the identity of a particular base, testing with all four nucleotides in succession may be needed. It is noted that statistically, at the introduction of each nucleotide, only about a quarter of the nucleic acid molecules contain a match, and are progressed, the remainder will remain inert until the addition of the matching nucleotide. Thus, a process that uses four distinct labels for the four nucleotides is more efficient.

To detect the nucleotide sequence while it is held by polymerase in the closed complex state, the detection step is performed before the addition of the divalent cation. It is noted that because, in many cases, the nucleic acid molecules sequenced are concentrated at discrete locations, the concentration of sequestered labeled nucleotides is higher than the free floating nucleotides. If the detection system is site-specific and sensitive enough, and the free floating, labeled nucleotide is at a sufficiently low concentration, it is possible to detect the nucleotides in the closed complex without the removal of unbound nucleotides.

Another way to detect the nucleotide incorporation event is to detect reaction by-products after incorporation of the nucleotide into the growing chain. The nucleotide may contain an enzyme activatable label on the terminal phosphate. After polymerization, the enzyme activatable label is present on the inorganic polyphosphate by-product. Cleavage of the polyphosphate by-product by phosphatase could generate a detectable label. If the labels are distinct for each nucleotide, all four nucleotides can be distinguished in the same reaction. If the labels are not distinct, each nucleotide is introduced separately, to distinguish the different nucleotides. Alternatively, PPi released from the un-labeled nucleotide during polymerization reaction can be detected by a variety of assay methods, although cycling is necessary to distinguish each base. One such assay is accomplished by detecting photon emission through a cascade of reactions: ATP sulfurylase is first used to generate ATP from PPi and adenosine-5'-phosphosulfate; then luciferase converts the ATP and luciferin to oxyluciferin, emitting a photon. Nyren et al., 151 Analytical Biochemistry 504 (1985).

For parallel sequencing, the ternary complex of polymerase-template-nucleotide can be immobilized on beads or other devices within confined locations of a carrier (e.g. a well), or they can be immobilized directly to the surface of a microscope slide or the like. The surface of a microscope slide can be a planar surface, or a coated surface. One example of a coated surface is described in a recent publication by Shendure et al. (Science, published online Aug. 4, 2005, 10.1126/science.1117389). The authors used an improved polyacrylamide gel and managed to ensure that beads are settled in a single focal plane at the surface of the gel.

When the support surface is in the form of a bead, it can take multiple forms as well. Streptavidin-coated sepharose beads have been used to immobilize PCR amplified, biotinylated single stranded DNA. Based on this technology, a 96 well plate format pyrosequencing platform is developed and commercialized by Biotage AB. Each well of a 96 well plate contains beads carrying a single type of single stranded template DNA. Using this platform, 96 reactions can be carried out at the same time. The combination of the 96-well format, with the closed complex formation, provides improved, accurate sequencing results not achievable by the conventional pyrosequencing technique.

Another bead based pyrosequencing platform is recently developed by 454 Life Sciences Corp. Margulies et al., *Nature* advance online publication; published online 31 Jul. 2005, doi: 10.1038/nature03959, incorporated by reference in its entirety. These microbeads are deposited in tiny, picoliter sized wells of a fibre-optic slide, each well can only accomodate a single bead. Each bead carries multiple nucleic acid templates of the same kind (i.e. same sequence), amplified by emulsion PCR. In their system, each bead is surrounded by even smaller beads carrying enzymes required for the pyrophosphate detection. A flow-through system is developed that allows efficient reagent flow and simultaneous extension reactions on each of the template-carrying beads. The light generated by luciferase reaction is detected as well as the position of the well, such that a correlation provides the sequence readout for a particular DNA on a bead in a well at a fixed position. Although this platform offers high throughput parallel sequencing, it still is limited by the characteristics of the pyrosequencing methodology. In particular, there is interference when dNTPs, particularly dATP reacts directly with luciferase, and sequence runs of a strech of two or more of the same nucleotide base are only resolved by quantitative measurement of luminescence intensity.

Incorporation of the closed complex formation into the 454 Life Sciences Corp. microbead technology offers several advatages. Because un-bound nucleotides are removed before detection, non-specific reaction of the luciferase system is no longer an issue. Luciferase, like polymerase is not catalytically active in the absence of divalent cation. The closed complex system allows sequencing of a single base at a time, irrespective of the presence of a strech of two or more of the same nucleotide base in the template. Therefore, the signal emission strength does not need to be interpreted for detection of long stretches of the same base. For the same reason, the new method also minimizes the problem of losing synchronism (See Ronaghi, Genome Research, 11, 3-11, 2001). Also for the same reason, the new method combining pyrosequencing with closed complex formation solves the problem of the so called "blooming effect"—a phenomenon associated with increased light emission when a long stretch of the same base is detected, where light emission spills into adjacent wells, causing false positive readouts in them.

Figure 8:
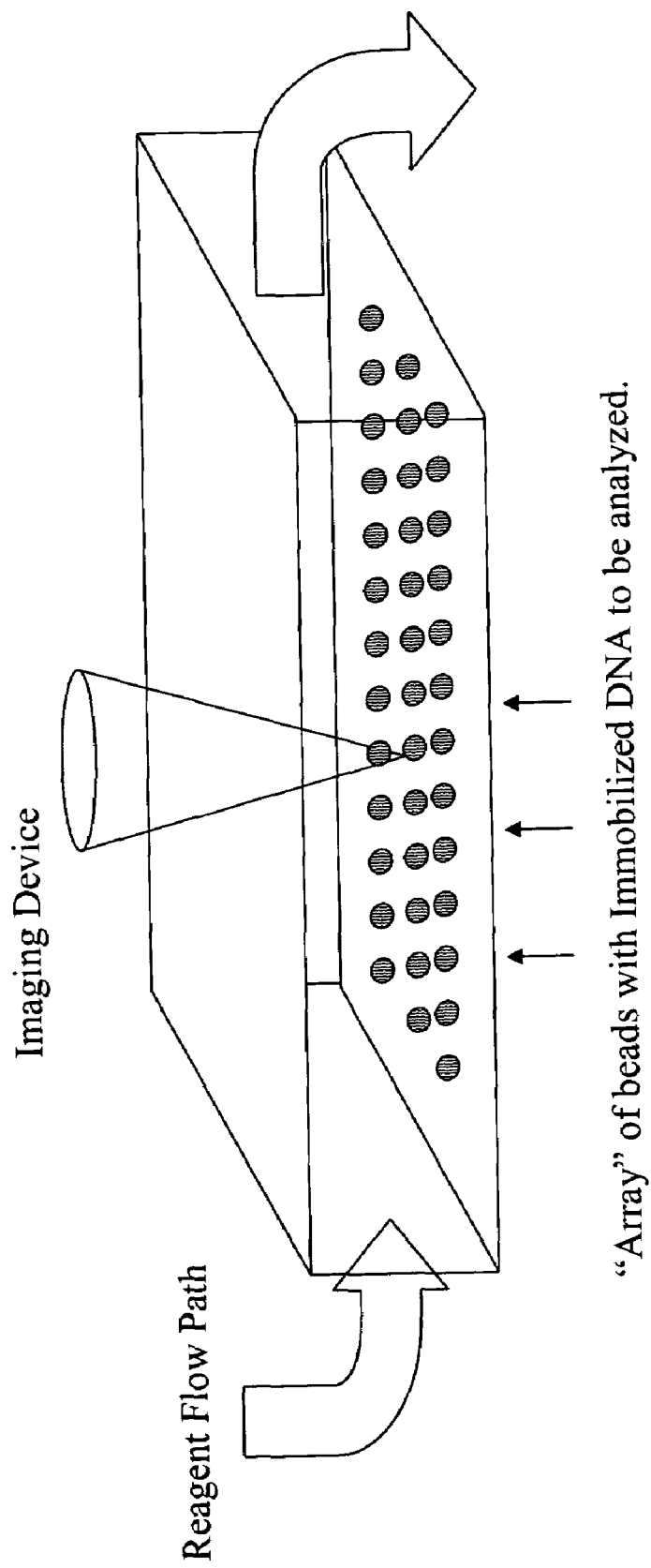
FIG. 8 depicts the reaction and detection scheme for sequencing with primed templates attached to individual beads.
Figure 9:
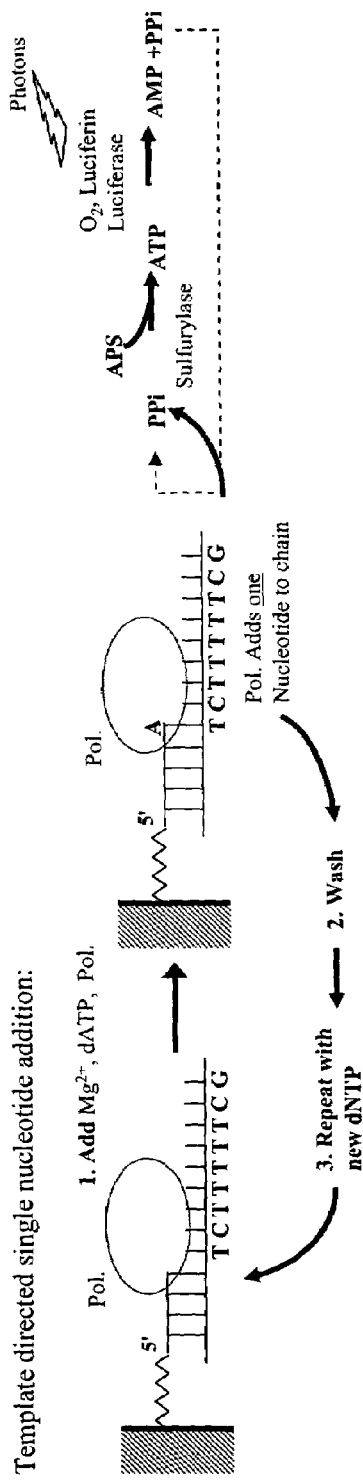
FIG. 9 depicts the reaction and detection scheme for sequencing by the pyrosequencing method.
Figure 9:
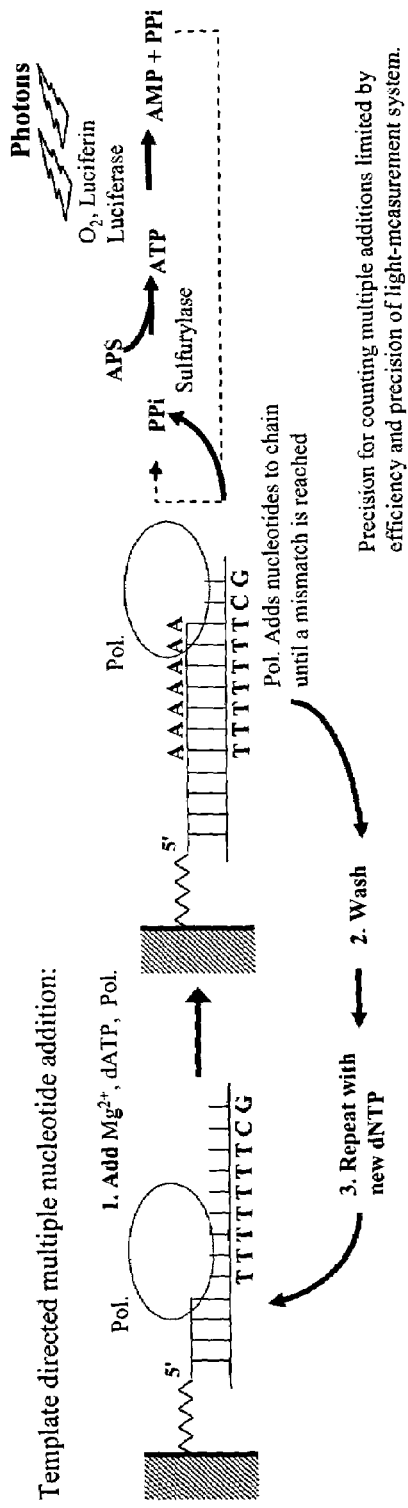

FIG. 8 depicts the general reaction and detection scheme for sequencing an array of beads, with primed templates attached to individual beads. FIG. 9 shows in detail the reaction and detection scheme for sequencing by the pyrosequencing method. Shown in the figure are two individual beads, one has a stretch of seven "T" nucleotides at the priming site (partial sequence shown as 5'-GCTTTTTTT-3' (SEQ ID NO: 5), shown in the 3' to 5' direction in the figure), the other has a single "T" followed by a different nucleotide (5'-GCTTTTTCT-3' (SEQ ID NO: 6)). In the presence of divalent cation and a single nucleotide (e.g. dATP), polymerase adds a nucleotide (e.g. A) complementary to the next template nucleotide (e.g. T), until the next template nucleotide base is not complementary to the nucleotide present (Seven "A" are added in the first situation, 5'-AAAAAAA-3' (SEQ ID NO: 7)). Nucleotide incorporation is detected, as an example, by the detection of photons generated from the Luciferase reaction following conversion of pyrophosphate product through a succession of enzymatic steps (Hyman U.S. Pat. No. 4,971,903). It is noted that the precision of detecting multiple nucleotide additions is limited by the efficiency and precision of the light-measurement system as well as the succession of enzymes needed to convert the pyrophosphate to the detected light output.

Figure 10A:
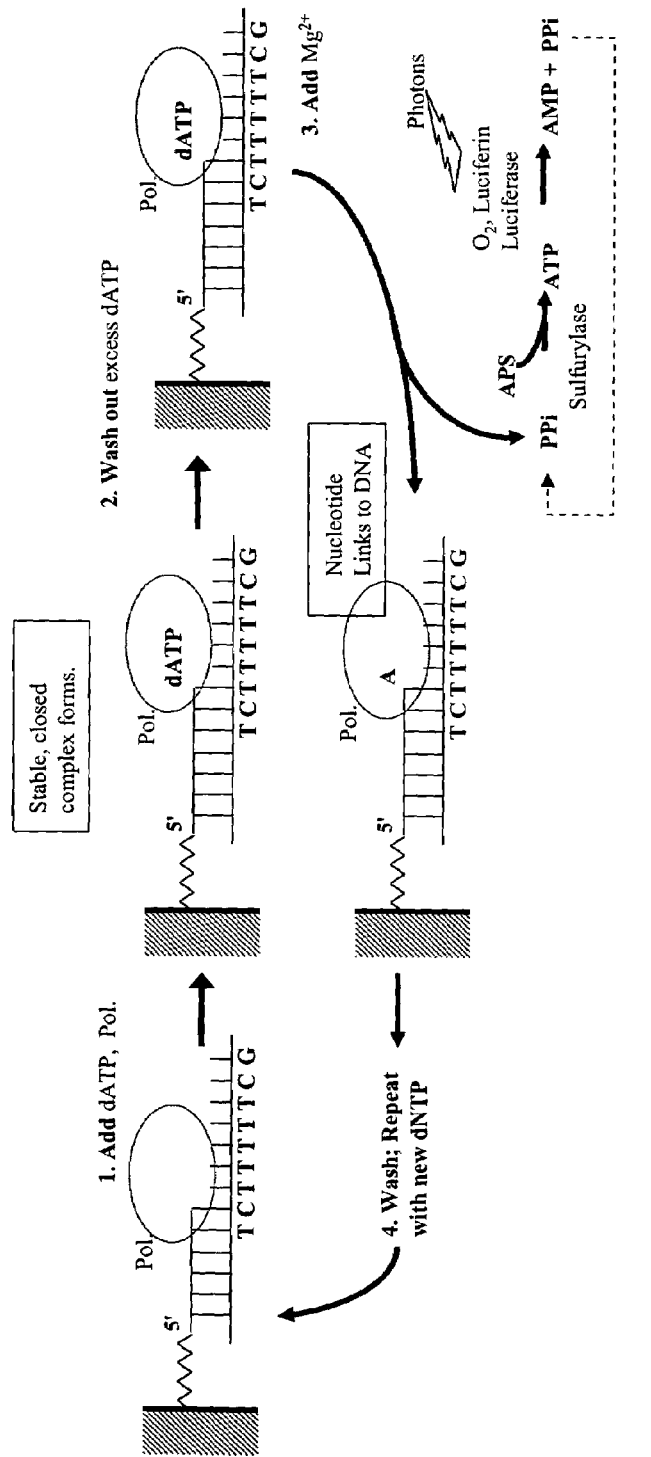
FIG. 10A and 10B depict the reaction and detection scheme for sequencing by the new, stepwise method with pyrophosphate detection.
Figure 10B:
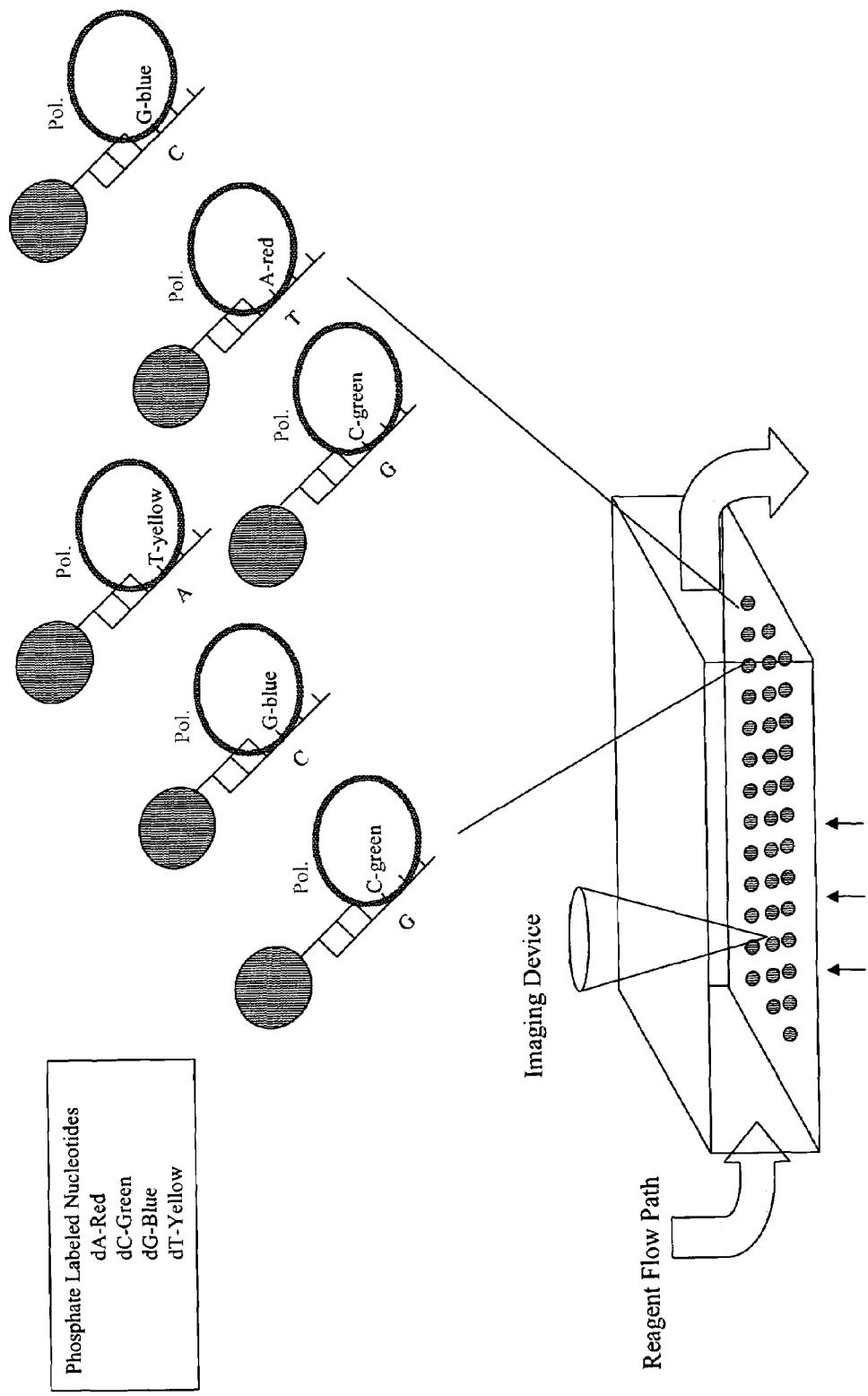

FIG. 10 depicts the reaction and detection scheme for sequencing by the new, stepwise method with pyrophosphate detection. FIG. 10A shows the reaction of an individual bead when one of four nucleotides is added to the reaction system. In the absence of divalent cation, polymerase forms a stable, closed-complex with the nucleotide (e.g. dATP) that complements the next template nucleotide (e.g. T, partial template sequence shown: 5'-GCTTTTTCT-3' (SEQ ID NO: 6)). Excess nucleotide is washed away. Then divalent cation is introduced along with other detection reagents and detection is performed, as an example, by the detection of photons generated from the Luciferase reaction through a succession of enzymatic steps. It is noted that because a closed-complex only forms with a complementary nucleotide, each cycle adds at most one nucleotide to the growing chain. FIG. 10B shows an alternative to FIG. 10A. Here terminal phosphate-labeled nucleotides are each labeled with a distinct label. In this way, all four nucleotide bases can be added in the same reaction mixture such that the next base of all the templates can be identified in a single round of polymerase reaction.

While the methods can be used to sequence unknown templates, it can also be used to confirm known sequences, identify single nucleotide polymorphisms, and perform single base extension reactions, amongst others. Double-ended sequencing can be used to sequence both ends of a template in a single well/bead/location. For a description of double ended sequencing, see supplemental information in Margulies et al., Nature advance online publication; published online 31 Jul. 2005, doi: 10.1038/nature03959.

The photons generated by luciferase can be detected by using a variety of detection apparatuses. A photomultiplier tube, an avalanche photodiode, a charge-coupled device (CCD), and a luminometer are a few examples. The dye labels from a closed complex can also be detected by a scanning microscope or fluorescence scanner or fluorescence microscope.

The data obtained from these methods are processed in a computer system with an appropriate algorithm. The data are converted to sequence information of each of the four nucleotides, either instantaneously as the data is generated, or at the end of the experimental process. The sequences may be assembled for each of the plurality of nucleic acid templates. It is noted that the order of addition of labeled nucleotides can occur in a preset cycle, but it is not essential.

EXAMPLES

The following examples present certain preferred embodiments of the instant invention but are not intended to be illustrative of all embodiments. These examples should not be construed as limiting the appended claims and/or the scope of this invention.

Example 1

Demonstration of the Formation of the "Closed Complex"

Figure 5:
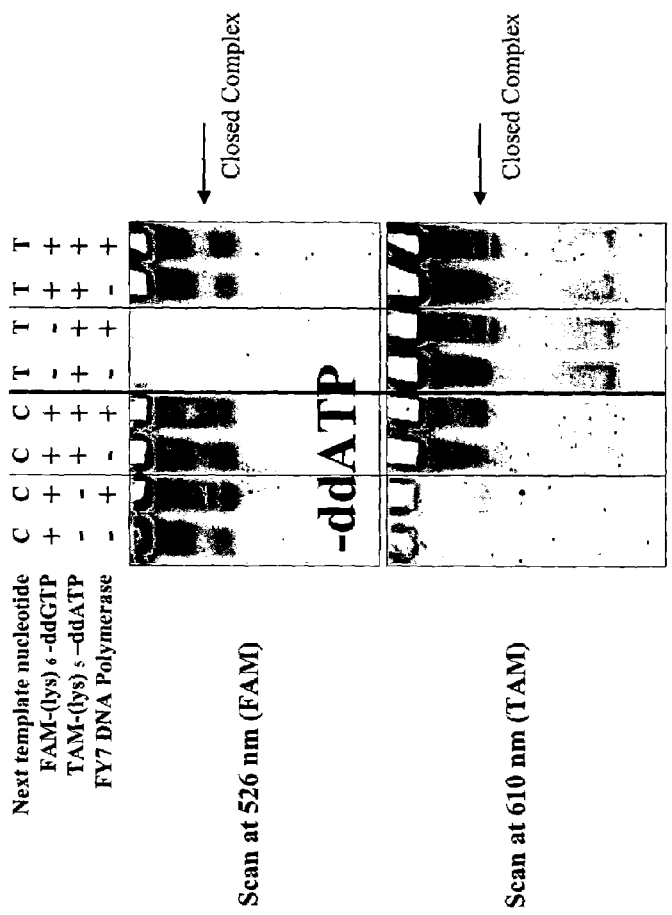
FIG. 5 presents evidence of the formation of the stable closed complex using fluorescently labeled nucleotides. It clearly demonstrates that the complex can be detected as described herein.

FIG. 5 presents evidence of the formation of this type of stable closed complex using fluorescently labeled nucleotides. It clearly demonstrates that the complex can be detected as described herein. Polymerase reactions (20 ul) were performed in (25 mM Tris:Borate, pH=7.5, 0.1 mM EDTA, 10% glycerol) and contained: 50 pmoles of primed template as indicated, +/−20 pmoles of labeled, positively charged ddGTP and/or ddATP; +/−3 pmoles FY7 DNA polymerase. Reaction products were separated on 7% PAGE in 50 mM Tris:Borate, pH=7.5. Complex formation is only observed when polymerase, primer template, and the correct nucleotide are present.

Figure 6:
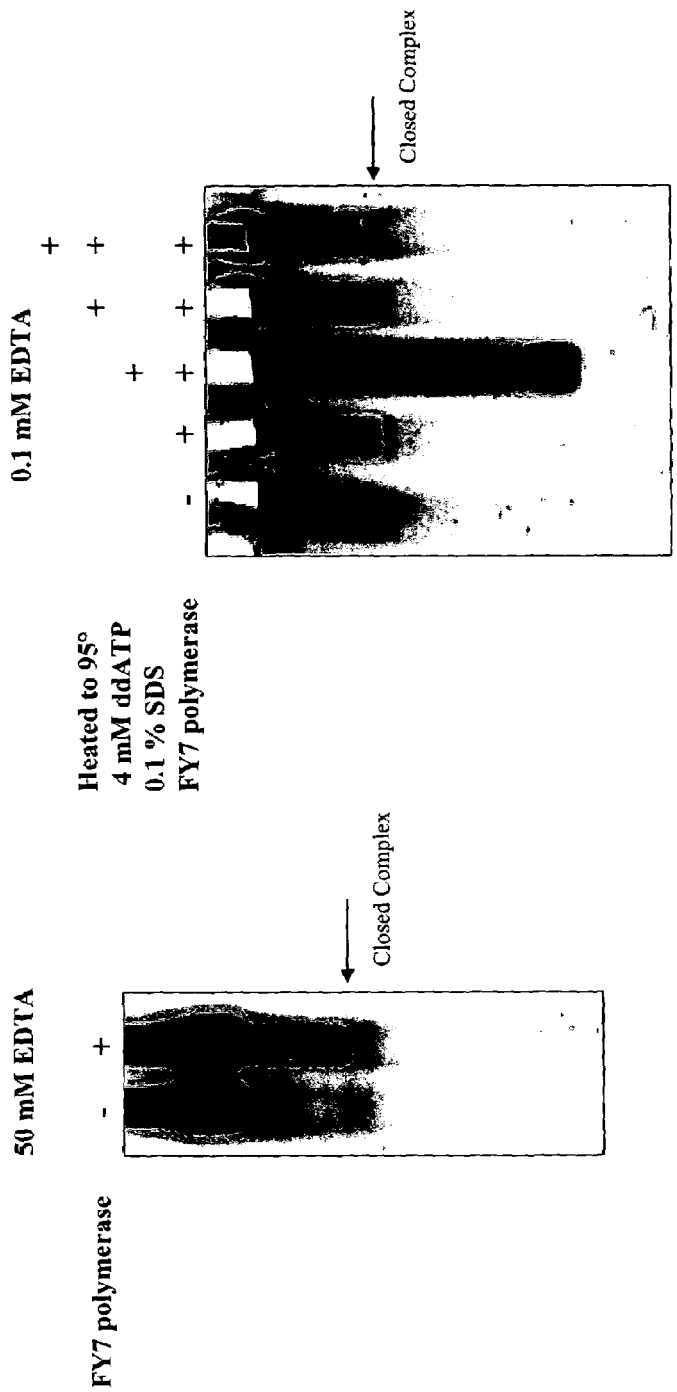
FIG. 6 demonstrates how SDS destroys the closed complex.

FIG. 6 demonstrates that the "closed complex" can be formed in up to 50 mM EDTA, can be destroyed with SDS, and competed with "cold" competitor. Reactions (20 ul) were performed in (25 mM Tris:Borate, pH=7.5, 50 or 0.1 mM EDTA as indicated on the Figure, and 10% glycerol) and contained: 50 pmoles of primed template with T as next template nucleotide, 20 pmoles of labeled, positively charged ddATP (next correct nucleotide), +/−3 pmoles FY7 DNA polymerase as indicated. After the complex was allowed to form, [4 mM ddATP]$_f$ was added as indicated on the Figure and the sample was heated to 95° for 30 seconds and allowed to cool before loading as indicated on the Figure. Reaction products were loaded and separated on a 7% PAGE in 50 mM Tris:Borate, pH=7.5. Closed complex of ddATP-template-FY7 DNA polymerase can be formed under 50 mM of EDTA and 0.1 mM of EDTA. Closed complex is destroyed, however, at the presence of 0.1% of SDS, and is competed with un-labeled "cold" ddATP.

Figure 7:
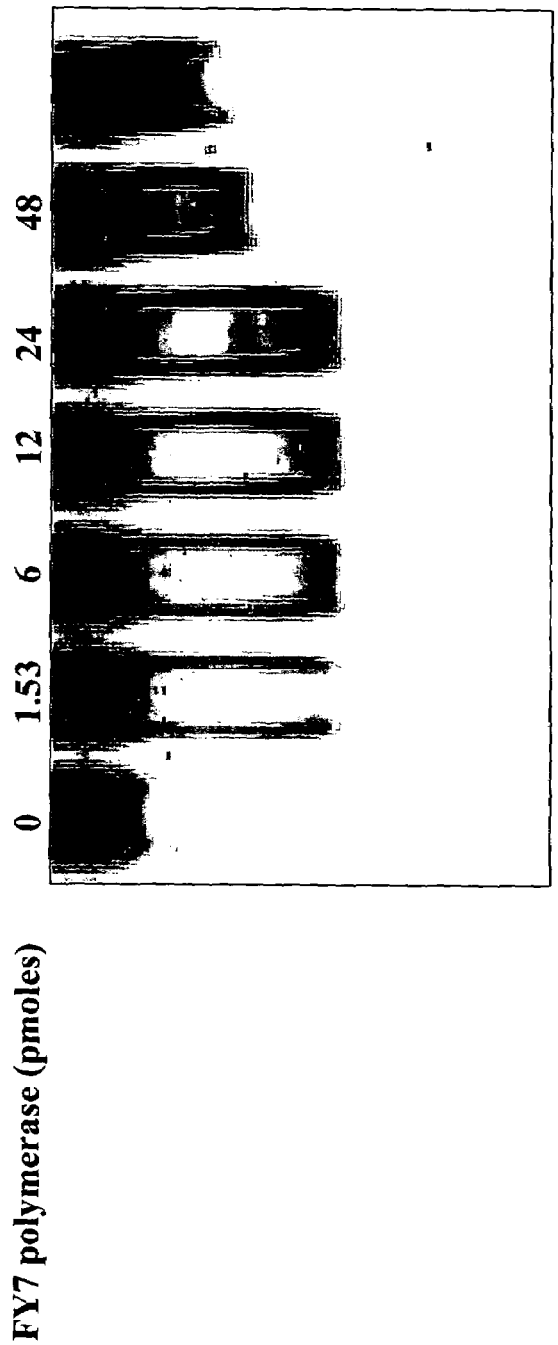
FIG. 7 demonstrates polymerase titration of the closed complex.

FIG. 7 demonstrates polymerase titration of the closed complex. Reactions (20 ul) were performed in (25 mM Tris:Borate, pH=7.5, 5 mM EDTA, 10% glycerol) and contained: 20 pmoles of primed template with T as next template nucleotide, 10 pmoles of labeled, positively charged ddATP (next correct nucleotide), and FY7 DNA polymerase as indicated. Reaction products were separated using 7% PAGE in 50 mM Tris:Borate, pH=7.5. Binding of next correct nucleotide by FY7 DNA polymerase forms a stable "closed complex" which can be isolated by non-denaturing PAGE. A close to linear increase of closed complex formation is observed with the increase of FY7 DNA polymerase.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for parallel sequencing of a plurality of nucleic acid templates, comprising:
   a) immobilizing a plurality of primed nucleic acid templates on a support structure, wherein each primed template includes a template and a primer, and is localized to an identifiable, discrete location on said support structure;
   b) initiating a plurality of complexation reactions on said support structure, by forming a reaction mixture, said reaction mixture including said plurality of primed templates, a nucleic acid polymerizing enzyme, and at least one nucleotide to form a plurality of closed complexes, each comprising one of said plurality of primed templates, said nucleic acid polymerizing enzyme, and one of said at least one nucleotide, wherein said nucleotide contains a base that complements the template base at the site of polymerization;
   c) removing unbound nucleotide and other unbound components of said reaction mixture;
   d) adding a divalent cation to complete the reaction;
   e) detecting, at each of said identifiable, discrete locations, incorporated nucleotide or other reaction product for each closed complex;
   f) removing said divalent cation and other end products; and
   g) repeating steps b) through f) for the sequencing of each additional nucleotide of said plurality of primed templates.

2. The method of claim 1, wherein said support structure comprises beads, and wherein said beads carry a single primer template combination and is identifiably separated from beads carrying a different primer template combination.

3. The method of claim 2, wherein said templates are immobilized to said beads by polymerase colony technology.

4. The method of claim 2, wherein said beads are supported in individual wells of a multi-well plate and said beads are separated into said individual wells.

5. The method of claim 1, wherein said identifiable, discrete locations are individual wells of a 96 well plate, and up to 96 parallel sequencing reactions are performed simultaneously.

6. The method of claim 1, wherein said identifiable, discrete locations are individual wells of a 384 well plate, and up to 384 parallel sequencing reactions are performed simultaneously.

7. The method of claim 1, wherein said identifiable, discrete locations are individual wells of a 1536 well plate, and up to 1536 parallel sequencing reactions are performed simultaneously.

8. The method of claim 2, wherein each bead is separated by deposition into a well of a fibre-optic slide.

9. The method of claim 8, wherein each well of said fibre-optic slide holds a single bead.

10. The method of claim 1, wherein said support structure is a first surface of a glass slide.

11. The method of claim 1, wherein said reaction mixture in said step (b) further includes EDTA or other chelating agent.

12. The claim of claim 1, wherein said nucleic acid polymerizing enzyme is selected from DNA polymerase or reverse transcriptase.

13. The method of claim 1, wherein said nucleic acid polymerizing enzyme is selected from DNA polymerase I, T4 DNA polymerase, Amplitaq FS, T7 DNA polymerase, Phi 29 DNA polymerase, Klenow exo⁻, Sequenase, Taq DNA polymerase, Thermo Sequenase I, ThermoSequenase II, FY7 DNA polymerase, ThemoSequenase E681M, *T. hypogea* (Thy B) DNA polymerase, *T. neapolitana*(Tne) DNA polymerase, *T. subterranea* (Tsu) DNA polymerase, *T. barossii* (Tha) DNA polymerase, *T. litoralis* (Vent) DNA polymerase, *T. kodakaraensis* DNA polymerase, *P. furiosis* DNA polymerase, P. GB-D (Deep Vent) DNA polymerase, Human Pol beta, Tsp JS1 DNA polymerase, AMV-reverse transcriptase, MMLV-reverse transcriptase and HIV-reverse transcriptase, or exonuclease deficient variants of these polymerases.

14. The method of claim 1, wherein said at least one nucleotide is labeled on the terminal phosphate.

15. The method of claim 14, wherein said detecting step (e) is performed before said adding step (d), wherein each different nucleotide carries a distinct label, and wherein said detecting step is performed by detecting, at each location, said distinct label from said terminal phosphate labeled nucleotide.

16. The method of claim 14, wherein each of said at least one nucleotide are four nucleotides, each carries a distinct label and complements one of the four naturally occurring bases.

17. The method of claim 14, wherein said labels in said terminal-phosphate-labeled nucleotides are fluorescent dyes, colored dyes, or chemiluminescent moieties.

18. The method of claim 17, wherein said fluorescent dyes are selected from the group consisting of a xanthene dye, a cyanine dye, a merrocyanine dye, an azo dye, a porphyrin dye, a coumarin dye, a bodipy dye and derivatives thereof.

19. The method of claim 17, wherein said colored dyes are selected from the group consisting of an azo dye, a merrocyanine, a cyanine dye, a xanthene dye, a porphyrin dye, a coumarin dye, a bodipy dye and derivatives thereof.

20. The method of claim 14, wherein said label is an enzyme activatable label present on the inorganic polyphosphate by-product of polymerization reaction, and said detecting step further includes cleavage of said polyphosphate by-product by phosphatase to generate a detectable label.

21. The method of claim 1, wherein said detecting step (e) is performed by measuring inorganic polyphosphate released from said nucleotide and inferring identity of the nucleotide base.

22. The method of claim 21, wherein said detecting step is performed by measuring photons, wherein said polyphosphate is pyrophosphate that is first converted to ATP by ATP sulfurylase, then a luciferase reaction generates said photons.

23. The method of claim 1, wherein said divalent cation is magnesium ($Mg^{2+}$).

24. The method of claim 1, wherein said divalent cation is manganese ($Mn^{2+}$).

25. The method of claim 1, wherein in step (a), said primed nucleic acid templates are formed prior to immobilization to said support structure.

26. The method of claim 1, wherein in step (a), said nucleic acid template is first immobilized to said support structure, then forms a primed nucleic acid template with said primer.

27. The method of claim 1, wherein in step (a), said primer is first immobilized to said support structure, then forms a primed nucleic acid template with said nucleic acid template.

* * * * *

SEQUENCE LISTING

<160> NUMBER OF SEQ ID NOS: 7

<210> SEQ ID NO 1
<211> LENGTH: 12
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 1
gggtttcctc tc                                                          12

<210> SEQ ID NO 2
<211> LENGTH: 7
<212> TYPE: DNA
<213> ORGANISM: ARTIFICIAL SEQUENCE
<220> FEATURE:
<223> OTHER INFORMATION: SYNTHETIC OLIGONULCEOTIDE

<400> SEQUENCE: 2 gtctctc                                                                 7

<210> SEQ ID NO 3
<211> LENGTH: 13
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 3
ctctcctttt ggg                                                         13

<210> SEQ ID NO 4
<211> LENGTH: 7
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 4 ctctctg                                                                 7

<210> SEQ ID NO 5
<211> LENGTH: 9
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 5 gctttttt                                                                9

<210> SEQ ID NO 6
<211> LENGTH: 9
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 6 gcttttttct                                                              9

<210> SEQ ID NO 7
<211> LENGTH: 7

```
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 7 aaaaaaa                                                              7
```